(12) United States Patent
McLaughlin et al.

(10) Patent No.: US 9,913,984 B2
(45) Date of Patent: Mar. 13, 2018

(54) STIMULATION CONFIGURATION MANAGEMENT SYSTEMS AND METHODS

(71) Applicant: ADVANCED BIONICS AG, Staefa (CH)

(72) Inventors: Myles McLaughlin, Santa Clarita, CA (US); Melanie Lucile Gilbert, Stevenson Ranch, CA (US)

(73) Assignee: Advanced Bionics AG, Staefa (CH)

( * ) Notice: Subject to any disclaimer, the term of this patent is extended or adjusted under 35 U.S.C. 154(b) by 6 days.

(21) Appl. No.: 15/024,028

(22) PCT Filed: Feb. 28, 2014

(86) PCT No.: PCT/US2014/019674
§ 371 (c)(1),
(2) Date: Mar. 22, 2016

(87) PCT Pub. No.: WO2015/130319
PCT Pub. Date: Sep. 3, 2015

(65) Prior Publication Data
US 2016/0228704 A1  Aug. 11, 2016

(51) Int. Cl.
*A61N 1/36* (2006.01)
*A61N 1/05* (2006.01)
*A61N 1/372* (2006.01)

(52) U.S. Cl.
CPC ....... *A61N 1/36032* (2013.01); *A61N 1/0541* (2013.01); *A61N 1/36036* (2017.08); *A61N 1/37235* (2013.01)

(58) Field of Classification Search
CPC .............. A61N 1/0541; A61N 1/37235; A61N 1/36032
See application file for complete search history.

(56) References Cited

U.S. PATENT DOCUMENTS 7,107,101 B1 * 9/2006 Faltys ................ A61N 1/36032
607/55
7,110,821 B1 9/2006 Ross
(Continued)

FOREIGN PATENT DOCUMENTS

WO   WO-2010/091177    8/2010

OTHER PUBLICATIONS

International Search Report and Written Opinion received in International Application No. PCT/US14/019674, dated Sep. 4, 2014.

*Primary Examiner* — Alyssa M Alter
(74) *Attorney, Agent, or Firm* — ALG Intellectual Property, LLC

(57) ABSTRACT

An exemplary stimulation configuration management system may 1) obtain electric field imaging (EFI) data for a plurality of stimulation configurations associated with an electrode included in an intracochlear electrode array that is a part of a cochlear implant system associated with a patient, 2) identify, based on the EFI data, a stimulation configuration included in the plurality of stimulation configuration and that focuses an electric field produced by current applied to the electrode more than any other stimulation configuration included in the plurality of stimulation configurations, and 3) direct the cochlear implant system to use the identified stimulation configuration for the electrode during a normal operation of the cochlear implant system.

19 Claims, 11 Drawing Sheets

(56) References Cited

U.S. PATENT DOCUMENTS

| | | |
|---|---|---|
| 7,340,308 B1 | 3/2008 | Clopton et al. |
| 7,769,467 B1 | 8/2010 | Emadi et al. |
| 7,860,573 B2 | 12/2010 | van den Honert |
| 8,532,781 B1 | 9/2013 | Vanpoucke |
| 2006/0247735 A1 | 11/2006 | Honert |
| 2009/0132006 A1 | 5/2009 | van den Honert et al. |
| 2011/0077710 A1 | 3/2011 | Saoji et al. |
| 2013/0204326 A1 | 8/2013 | Vanpoucke |

* cited by examiner

STIMULATION CONFIGURATION MANAGEMENT SYSTEMS AND METHODS

BACKGROUND INFORMATION

Cochlear implants often operate in a monopolar stimulation configuration, with current being sent out on an intracochlear electrode and returned via a distant extra-cochlear ground electrode. A monopolar stimulation configuration produces a relatively wide excitation pattern, does not allow for control of current flow within the cochlea, and often produces unwanted percepts. Multipolar stimulation configurations (e.g., partial tripolar stimulation configurations where current is sent out via an intracochlear electrode, a portion of the current is returned via two flanking intracochlear electrodes, and a remaining portion of the current is returned via the extra-cochlear ground electrode) may focus the electric field produced by current applied to an electrode (i.e., minimize current spread within the cochlea) and thereby result in better control of current flow, reduce unwanted percepts, and improve speech perception.

Unfortunately, it has been discovered that, in some patients, multipolar stimulation configurations actually result in broader, not narrower, excitation fields compared to monopolar stimulation configurations. This is likely due to the fact that the amount of current required to achieve a most comfortable stimulation level ("M level") associated with an electrode increases exponentially with the amount of focusing used with respect to the electrode. Hence, if a particular electrode within a patient is not positioned correctly, or if neural survival within a region associated with the electrode requires a relatively high current to achieve an M level associated with the electrode, a monopolar stimulation configuration may actually result in a narrower electric field than a multipolar stimulation configuration.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
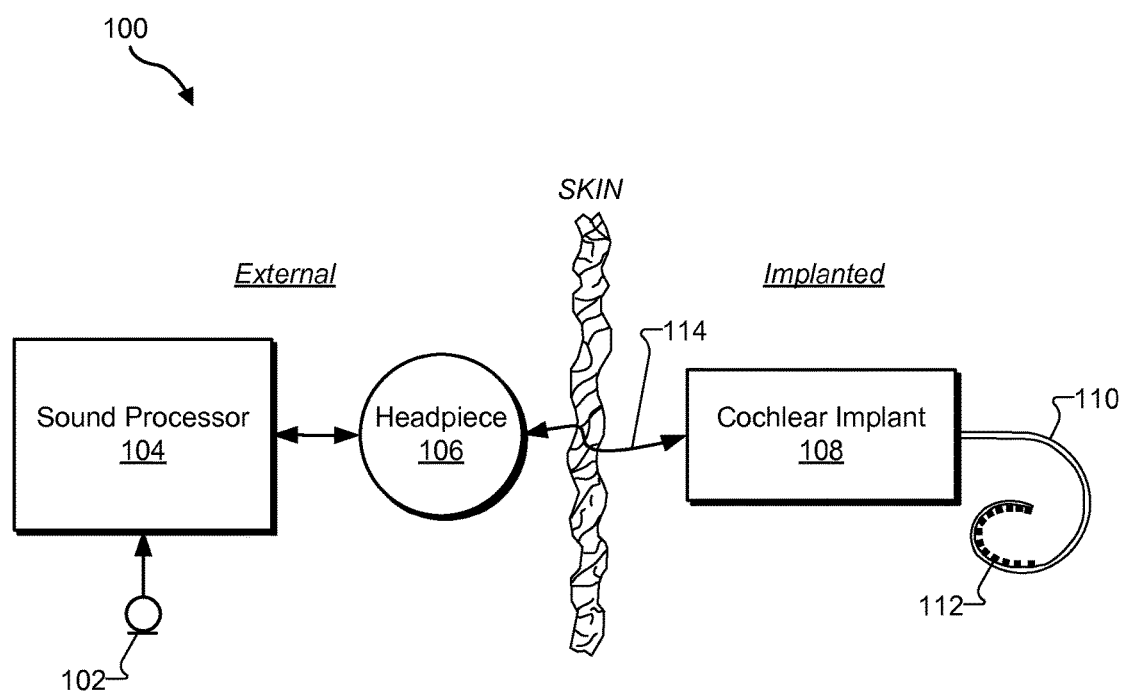
FIG. 1 illustrates an exemplary cochlear implant system according to principles described herein.

Stimulation configuration management systems and methods are described herein. As will be described below, a stimulation configuration management system may 1) obtain electric field imaging ("EFI") data for a plurality of stimulation configurations associated with an electrode included in an intracochlear electrode array that is a part of a cochlear implant system associated with a patient, 2) identify, based on the EFI data, a stimulation configuration included in the plurality of stimulation configuration and that focuses an electric field produced by current applied to the electrode more than any other stimulation configuration included in the plurality of stimulation configurations, and 3) direct the cochlear implant system to use the identified stimulation configuration for the electrode during a normal operation of the cochlear implant system.

To illustrate, the stimulation configuration management system may use any suitable EFI technique to obtain a first EFI data set for a monopolar stimulation configuration associated with the electrode and a second EFI data set for a multipolar stimulation configuration (e.g., a partial tripolar stimulation configuration) associated with the electrode. The stimulation configuration management system may then scale the first electric field data set to a first M level associated with both the electrode and the monopolar stimulation configuration and scale the second electric field data set to a second M level associated with both the electrode and the multipolar stimulation configuration. The stimulation configuration management system may then compare the scaled first electric field data set to the scaled second electric field data set to determine which stimulation configuration maximally focuses an electric field produced by current applied to the electrode. If the scaled first electric field data set is lower in amplitude than the scaled second electric field data set, the stimulation configuration management system may determine that the monopolar stimulation configuration maximally focuses the electric field and may accordingly direct the cochlear implant system to use the monopolar stimulation configuration for the electrode during a normal operation of the cochlear implant system. Alternatively, if the scaled second electric field data set is lower in amplitude than the scaled first electric field data set, the stimulation configuration management system may determine that the multipolar stimulation configuration maximally focuses the electric field and may accordingly direct the cochlear implant system to use the multipolar stimulation configuration for the electrode during the normal operation of the cochlear implant system.

The systems and methods described herein may facilitate selection of an optimal stimulation configuration for a particular electrode within a particular patient. For example, the systems and methods described herein may result in monopolar stimulation configurations being used for some electrodes in an intracochlear electrode array and different types of multipolar configurations being used for other electrodes in the same intracochlear electrode array. This may result in optimal focusing for each electrode and may be beneficial compared to scenarios in which a particular stimulation configuration (e.g., a particular type of multipolar stimulation configuration) is used for each electrode within the intracochlear electrode array regardless of whether the stimulation configuration is optimal for each electrode.

As used herein, a "monopolar stimulation configuration" refers to a stimulation configuration in which stimulation current is passed through a single intracochlear electrode (i.e., an electrode that is implanted within the cochlea) and an extracochlear ground electrode (i.e., an electrode located outside the cochlea). In monopolar stimulation, all of the current flows between the intracochlear electrode and the extracochlear ground electrode.

As used herein, a "multipolar stimulation configuration" may refer to either a "full multipolar stimulation configuration" or a "partial multipolar stimulation configuration." A "full multipolar stimulation configuration" refers to a stimulation configuration in which stimulation current is simultaneously applied to a main intracochlear electrode and one or more intracochlear compensating electrodes without any of the stimulation current flowing to the extracochlear electrode. Hence, all of the current flows between the main intracochlear electrode and the one or more intracochlear compensating electrodes. Exemplary full multipolar stimulation configurations include, but are not limited to, full bipolar stimulation (where stimulation current is passed between two intracochlear electrodes), full tripolar stimulation (where stimulation current is passed between three intracochlear electrodes), and full quadripolar stimulation (where stimulation current is passed between four intracochlear electrodes).

As used herein, a "partial multipolar stimulation configuration" refers to a stimulation configuration in which stimulation current is applied to a main intracochlear electrode while compensating current opposite in phase to that of the stimulation current is simultaneously applied to one or more intracochlear compensating electrodes. In partial multipolar stimulation, the total amount of compensating current applied to the compensating electrodes is less than the total amount of stimulation current applied to the main electrode. The remaining amount of current flows to the extracochlear ground electrode. For example, the amount of stimulation current applied to the main electrode may be represented by $I_0$ and the amount of stimulation current applied to the compensating electrodes may be represented by $\sigma * I_0$ (i.e., $\sigma$ multiplied by $I_0$), where $\sigma$ is greater than zero and less than one. Hence, the remaining amount of current that flows to the extracochlear ground electrode may be represented by $(1-\sigma) * I_0$. An exemplary partial multipolar stimulation configuration is a partial tripolar stimulation configuration.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an intracochlear electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
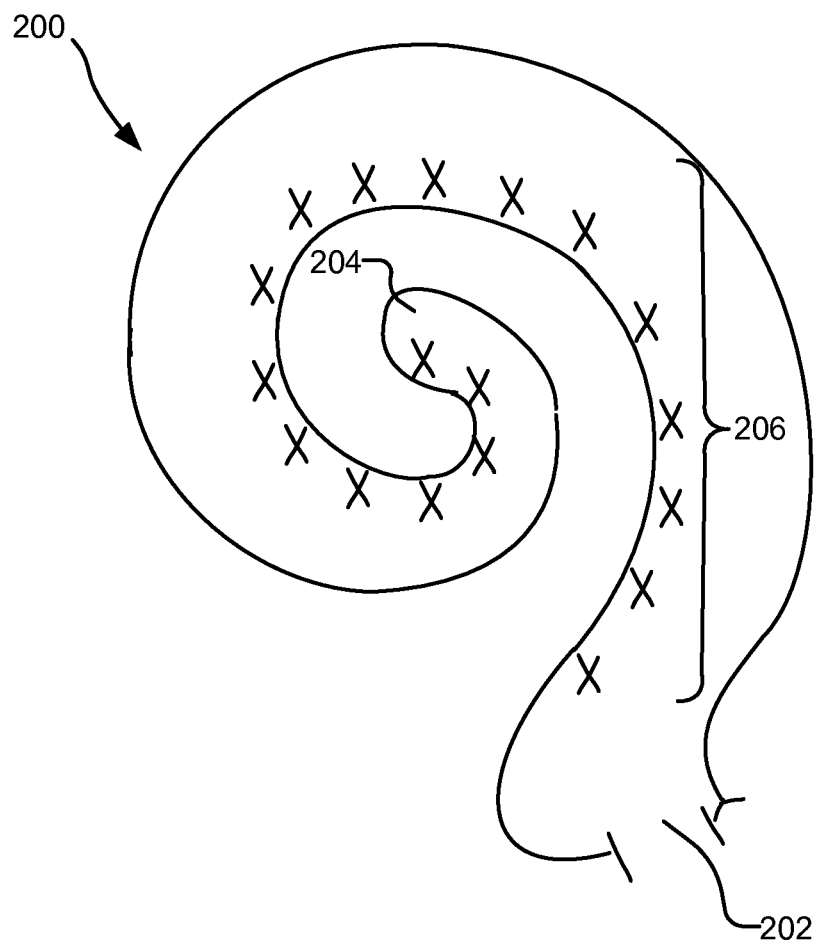
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
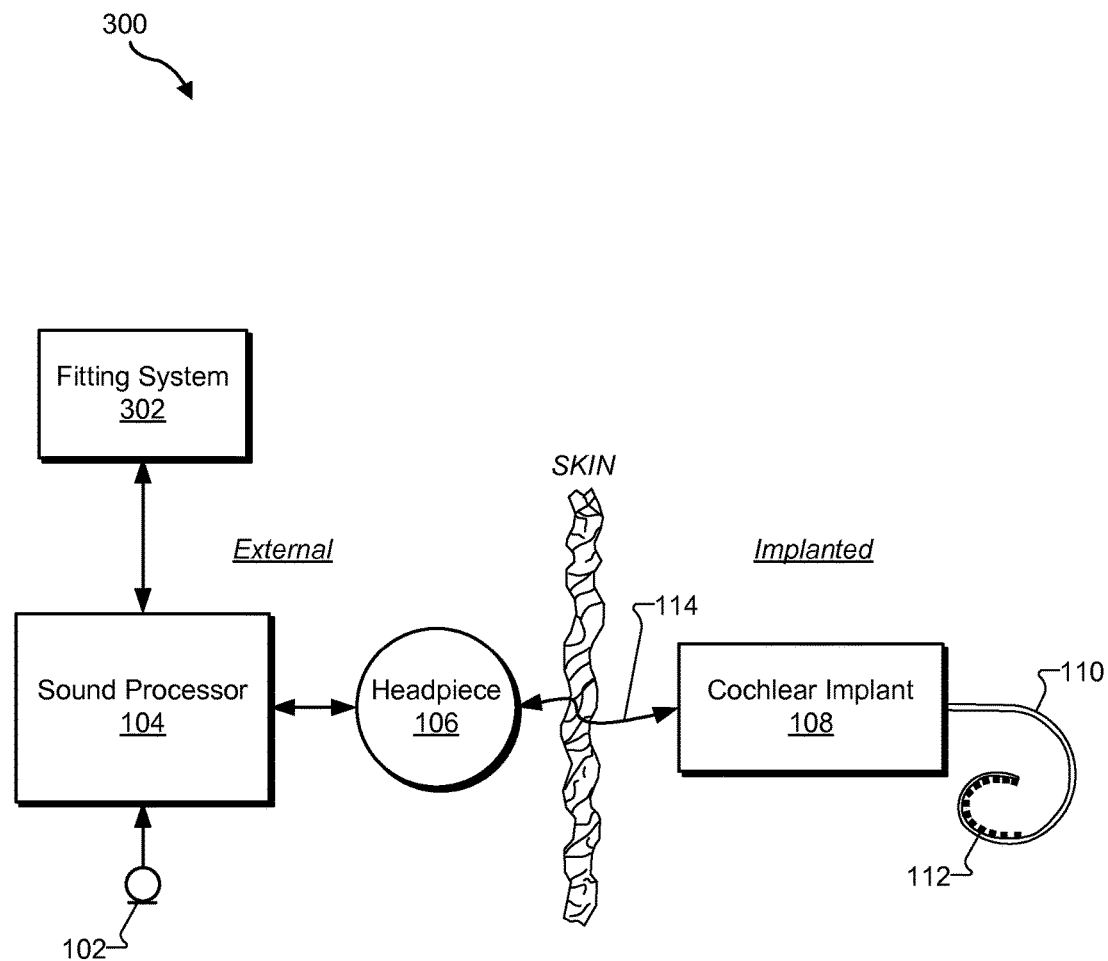
FIG. 3 shows an exemplary configuration in which a fitting system is communicatively coupled to the cochlear implant system shown in FIG. 1 according to principles described herein.

FIG. 3 shows an exemplary configuration 300 in which a fitting system 302 is communicatively coupled to cochlear implant system 100 by way of sound processor 104. Fitting system 302 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component or computing device as may serve a particular implementation. In some examples, fitting system 302 may provide one or more graphical user interfaces ("GUIs") (e.g., by presenting the one or more GUIs by way of a display screen) with which a clinician or other user may interact.

Fitting system 302 may be selectively coupled to sound processor 104 in any suitable manner. While coupled to sound processor 104, fitting system 302 may be used to perform various types of fitting procedures with respect to cochlear implant system 100. For example, fitting system 302 may program sound processor 104 to operate in accordance with one or more sound processing programs, adjust one or more control parameters associated with cochlear implant system 100, and/or perform any other suitable operation with respect to cochlear implant system 100. In some examples, fitting system 302 may perform any of the stimulation configuration management operations described herein.

Figure 4:
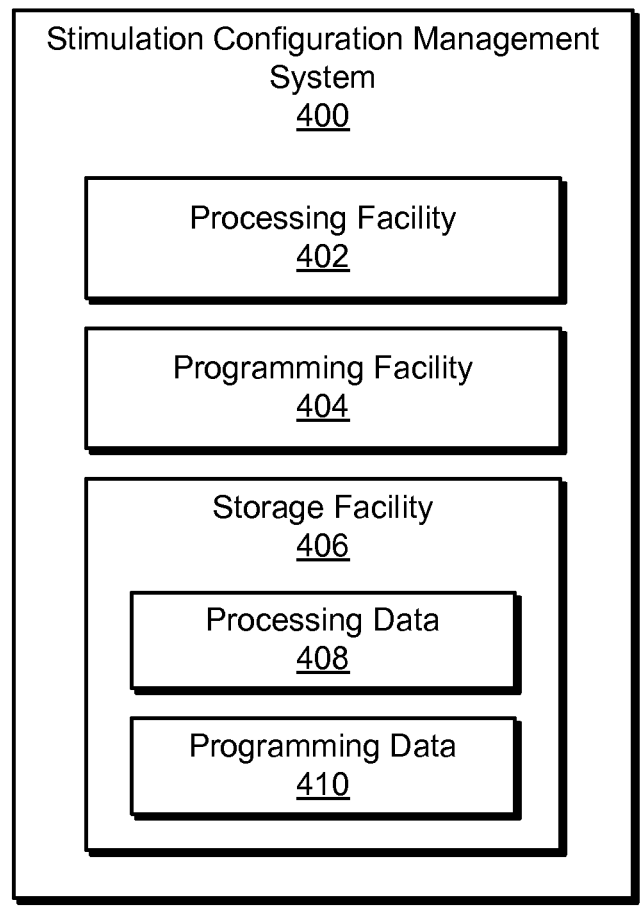
FIG. 4 illustrates an exemplary stimulation configuration management system according to principles described herein.

FIG. 4 illustrates an exemplary stimulation configuration management system 400 ("management system 400"). As shown, management system 400 may include a processing facility 402, a programming facility 404, and a storage facility 406, which may be in communication with one another using any suitable communication technologies. Storage facility 406 may be configured to maintain processing data 408 generated and/or used by processing facility 402, and programming data 410 generated and/or used by programming facility 404. Storage facility 406 may maintain additional or alternative data as may serve a particular implementation. One or more of facilities 402-406 may include or be implemented one or more computing devices and/or processors configured to perform one or more of the functions described herein.

Management system 400 (i.e., facilities 402-406) may be implemented by any suitable combination of components. For example, management system 400 may be entirely implemented by sound processor 104. In this manner, sound processor 104 may automatically select an optimal stimulation configuration for a particular electrode regardless of whether the patient is at a clinic participating in a fitting session. Alternatively, management system 400 may be entirely implemented by fitting system 302. In some examples, management system 400 may be implemented by a combination of sound processor 104 and fitting system 302.

Processing facility 402 may perform various stimulation configuration management operations with respect to a cochlear implant system (e.g., cochlear implant system 100). For example, processing facility 402 may obtain EFI data for a plurality of stimulation configurations associated with an electrode (e.g., an electrode 112) included in an intracochlear electrode array (e.g., electrode array 110) that is a part of a cochlear implant system (e.g., cochlear implant system 100) associated with a patient. As used herein, "EFI data" refers to data representative of intracochlear potentials (e.g., voltage levels) recorded by other electrodes included in the intracochlear electrode array that occur in response to stimulation of the electrode. The EFI data may be obtained in any suitable manner.

For example, processing facility 402 may obtain EFI data for a monopolar stimulation configuration associated with an electrode included in an intracochlear electrode array by directing a cochlear implant (e.g., cochlear implant 108) included in the cochlear implant system to apply a stimulation pulse to the electrode using the monopolar stimulation configuration. Processing facility 402 may then record an intracochlear potential that occurs in response to the stimulation pulse at each of a remaining number of electrodes in the intracochlear electrode array to obtain an EFI data set corresponding to the monopolar stimulation configuration. This process may be repeated for other stimulation configurations in order to obtain EFI data sets corresponding to each of the other stimulation configurations. Alternatively, as will be described below, once an EFI data set corresponding to a particular stimulation configuration (e.g., a monopolar stimulation configuration) is acquired, a linear model may be applied to the EFI data set in order to extrapolate one or more EFI data sets corresponding to one or more other stimulation configurations.

The electrode to which the stimulation pulse is applied in order to obtain EFI data is referred to herein as a "stimulating electrode". The electrodes used to record the intracochlear potentials that occur in response to the stimulation pulse being applied to the stimulating electrode are referred to herein as "recording electrodes."

In some examples, the stimulation pulse used to obtain the EFI data has a fixed amplitude (e.g., 100 microamps). As will be described below, EFI data sets obtained using the fixed amplitude stimulation pulse may be scaled to M levels associated with the electrode and the various stimulation configurations. Alternatively, the EFI data may be obtained using stimulation pulses that have amplitudes substantially equal to the M levels.

Figure 5:
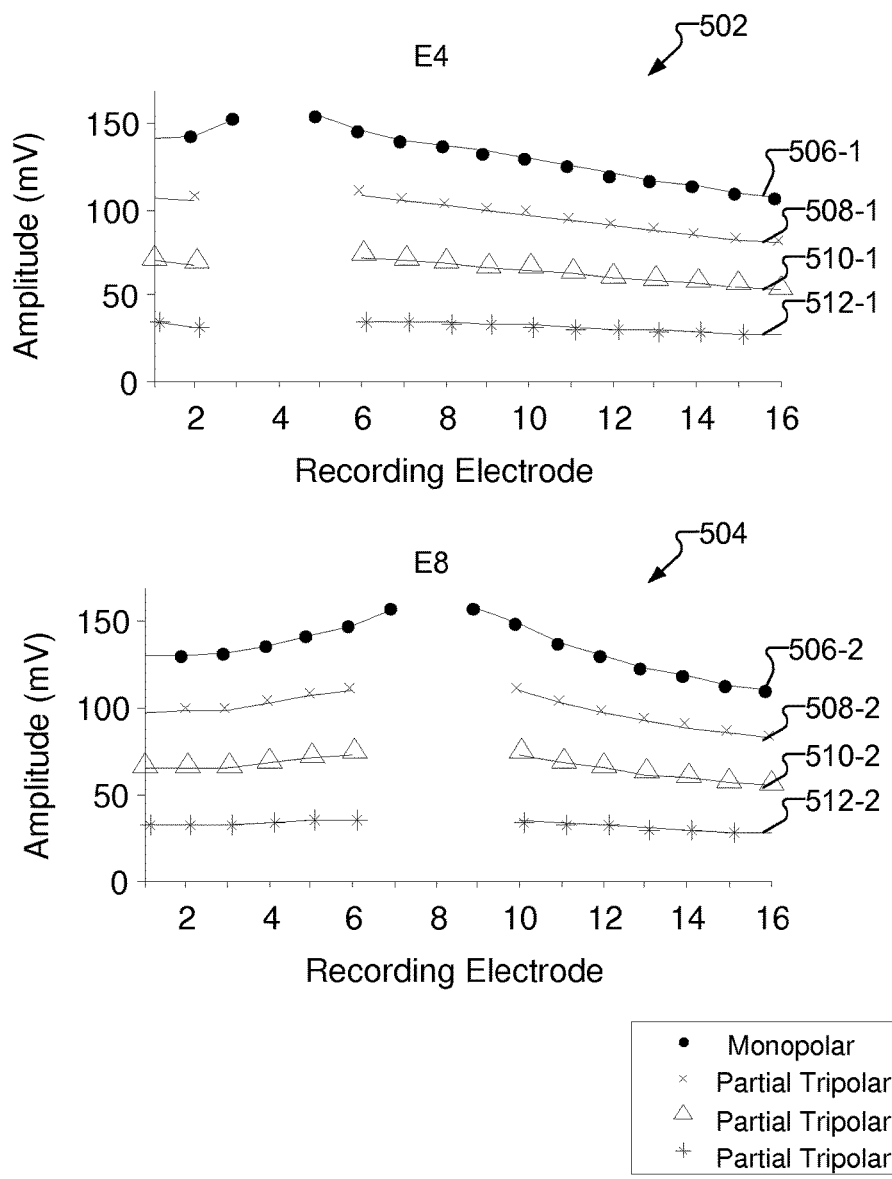
FIGS. 5-9 show graphs of various electric field imaging data sets and M levels according to principles described herein.

FIG. 5 shows graphs 502 and 504 of exemplary EFI data sets that may be obtained using a stimulation pulse having a fixed amplitude for a plurality of stimulation configurations associated with two different electrodes in an intracochlear electrode array that includes sixteen electrodes. It will be recognized that the EFI data sets illustrated in FIG. 5 are merely illustrative and that the intracochlear electrode array may alternatively include any other number of electrodes as may serve a particular implementation. Graph 502 corresponds to a fourth electrode (labeled "E4") included in the intracochlear electrode array and graph 504 corresponds to an eighth electrode (labeled "E8") included in the intracochlear electrode array.

As shown, each graph 502 and 504 includes EFI data sets corresponding to four different stimulation configurations: a monopolar stimulation configuration, a first partial tripolar stimulation configuration with σ equal to 0.25 (i.e., twenty-five percent of the current applied to a main electrode returns via two flanking electrodes), a second partial tripolar stimulation configuration with σ equal to 0.5 (i.e., fifty percent of the current applied to a main electrode returns via two flanking electrodes), and a third partial tripolar stimulation configuration with σ equal to 0.75 (i.e., seventy-five percent of the current applied to a main electrode returns via two flanking electrodes). The EFI data set corresponding to the monopolar stimulation configuration is represented in FIG. 5 by lines 506-1 and 506-2, the EFI data set corresponding to the first partial tripolar stimulation configuration is represented in FIG. 5 by lines 508-1 and 508-2, the EFI data set corresponding to the second partial tripolar stimulation configuration is represented in FIG. 5 by lines 510-1 and 510-2, and the EFI data set corresponding to the third partial tripolar stimulation configuration is represented in FIG. 5 by lines 512-1 and 512-2. Note that lines 506-512 are each discontinuous at a position that corresponds to the stimulating electrode (e.g., electrode 4 in graph 502 and electrode 9 in graph 504).

As shown, the EFI data may be different for each stimulation configuration and for each electrode. In the particular example of FIG. 5, the EFI data sets for the monopolar stimulation configuration have the highest overall amplitude and the EFI data sets for the third partial tripolar stimulation configuration have the lowest overall amplitude. This means that, for the stimulation pulse having the fixed amplitude, the monopolar stimulation configuration results in the least amount of electric field focusing out of the four stimulation configurations, while the third partial tripolar stimulation configuration results in the most amount of electric field focusing out of the four stimulation configurations.

The EFI data sets illustrated in FIG. 5 may be obtained in any suitable manner. For example, as described previously, each EFI data set may be acquired by applying a stimulation pulse to a desired electrode using a desired stimulation configuration and recording intracochlear potentials that occur in response to the stimulation pulse. Alternatively, as mentioned, a linear model may be applied to an EFI data set corresponding to a particular stimulation configuration (e.g., a monopolar stimulation configuration) in order to extrapolate one or more EFI data sets corresponding to one or more other stimulation configurations.

For example, with respect to graph 502, a linear model may be applied to the EFI data set represented by line 506-1 and corresponding to the monopolar stimulation configuration in order to extrapolate the EFI data sets represented by lines 508-1, 510-1, and 512-1 and corresponding to the partial tripolar stimulation configurations. For example, a linear model may be applied to the EFI data set corresponding to the monopolar stimulation configuration in accordance with the following equation: $Vtp_{i,j} = Vmp_{i,j} - (\sigma/2)*Vmp_{i-1,j} - (\sigma/2)*Vmp_{i+1,j}$.

In the preceding equation, $Vmp_{i,j}$ is the measured monopolar voltage matrix (i.e., the EFI data set corresponding to the monopolar stimulation configuration) and $Vtp_{i,j}$ is the predicted or extrapolated partial tripolar voltage matrix (i.e., the EFI data set corresponding to a desired partial tripolar stimulation configuration). Any other linear model may alternatively be applied to the EFI data set corresponding to the monopolar stimulation configuration as may serve a particular implementation.

In some examples, processing facility 402 may scale the EFI data sets obtained for a particular electrode using the fixed amplitude stimulation pulse to M levels associated with the electrode and with the various stimulation configurations. As used herein, an "M level" associated with an electrode refers to a stimulation current level applied by a cochlear implant system to the electrode at which the patient is most comfortable. M levels vary from patient to patient and from electrode to electrode. M levels also vary from stimulation configuration to stimulation configuration.

Figure 6:
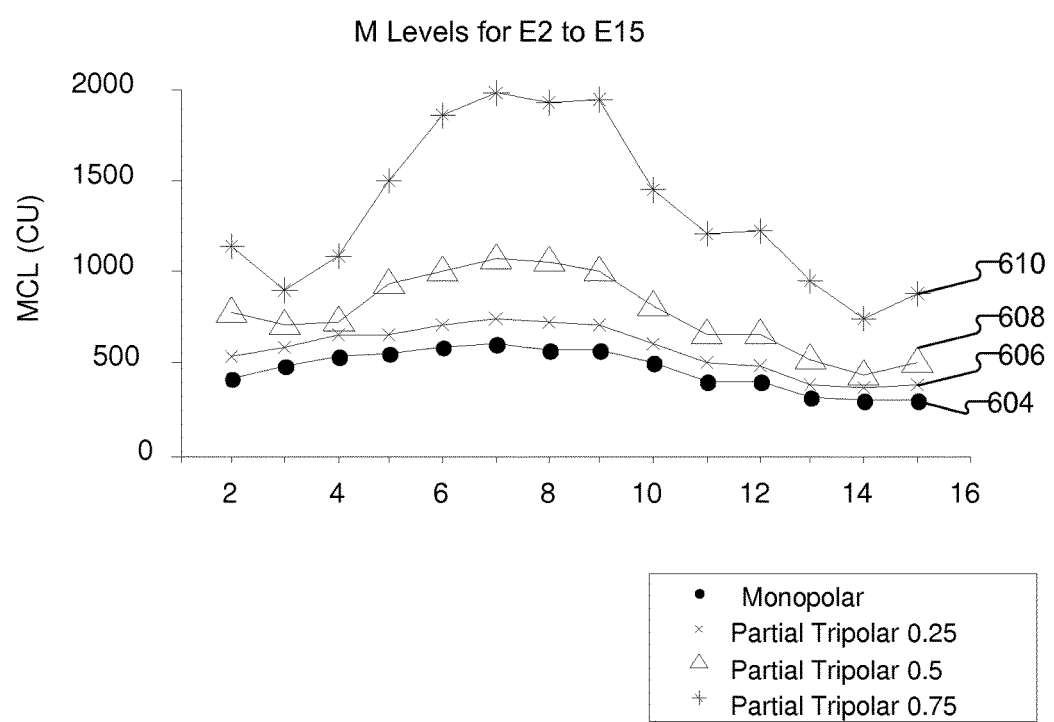

To illustrate, FIG. 6 shows a graph 602 that illustrates how M levels may vary by electrode and by stimulation configuration. The M levels corresponding to the monopolar stimulation configuration are represented in FIG. 6 by line 604, the M levels corresponding to the first partial tripolar stimulation configuration are represented in FIG. 6 by line 606, the M levels corresponding to the second partial tripolar stimulation configuration are represented in FIG. 6 by line 608, and the M levels corresponding to the third partial tripolar stimulation configuration are represented in FIG. 6 by line 610. As shown, the M levels are different for each electrode and for each stimulation configuration.

Processing facility 402 may determine the M levels in any suitable manner and at any suitable time (e.g., any time prior to scaling the EFI data sets to the M levels). For example, processing facility 402 may determine the M level for a particular electrode and stimulation configuration based on subjective feedback provided by the patient. For example, processing facility 402 may present various stimuli to a patient and then determine an M level based on an analysis of subjective feedback provided by the patient as to how the stimuli were perceived. Such subjective feedback may takes the form of either verbal (adult) or non-verbal (child) feedback.

Alternatively, processing facility 402 may objectively determine an M level for a particular electrode and stimulation configuration based on an evoked response that occurs in response to stimulation of the electrode. For example, processing facility 402 may stimulate the electrode using the stimulation configuration and measure an evoked neural response (e.g., from the auditory nerve, the brainstem, or the cortex) and/or a reflex (e.g., an electrical stapedius reflex). Processing facility 402 may then objectively determine the M level based on the evoked neural response and/or reflex.

Processing facility 402 may scale the EFI data sets obtained for a particular electrode using the fixed amplitude stimulation pulse to M levels associated with the electrode and the various stimulation configurations in any suitable manner. For example, processing facility 402 may scale an EFI data set to an M level in accordance with the following equation: $V_{scaled} = I_{M-level} * (V_{measured}/I_{stim})$. In this equation, $I_{stim}$ represents the fixed amplitude stimulation pulse, $I_{M-level}$ represents the M level for the appropriate stimulation configuration, $V_{measured}$ represents the measured intracochlear potential, and $V_{scaled}$ represents the intracochlear potential after it has been scaled to the M level.

Figure 7:
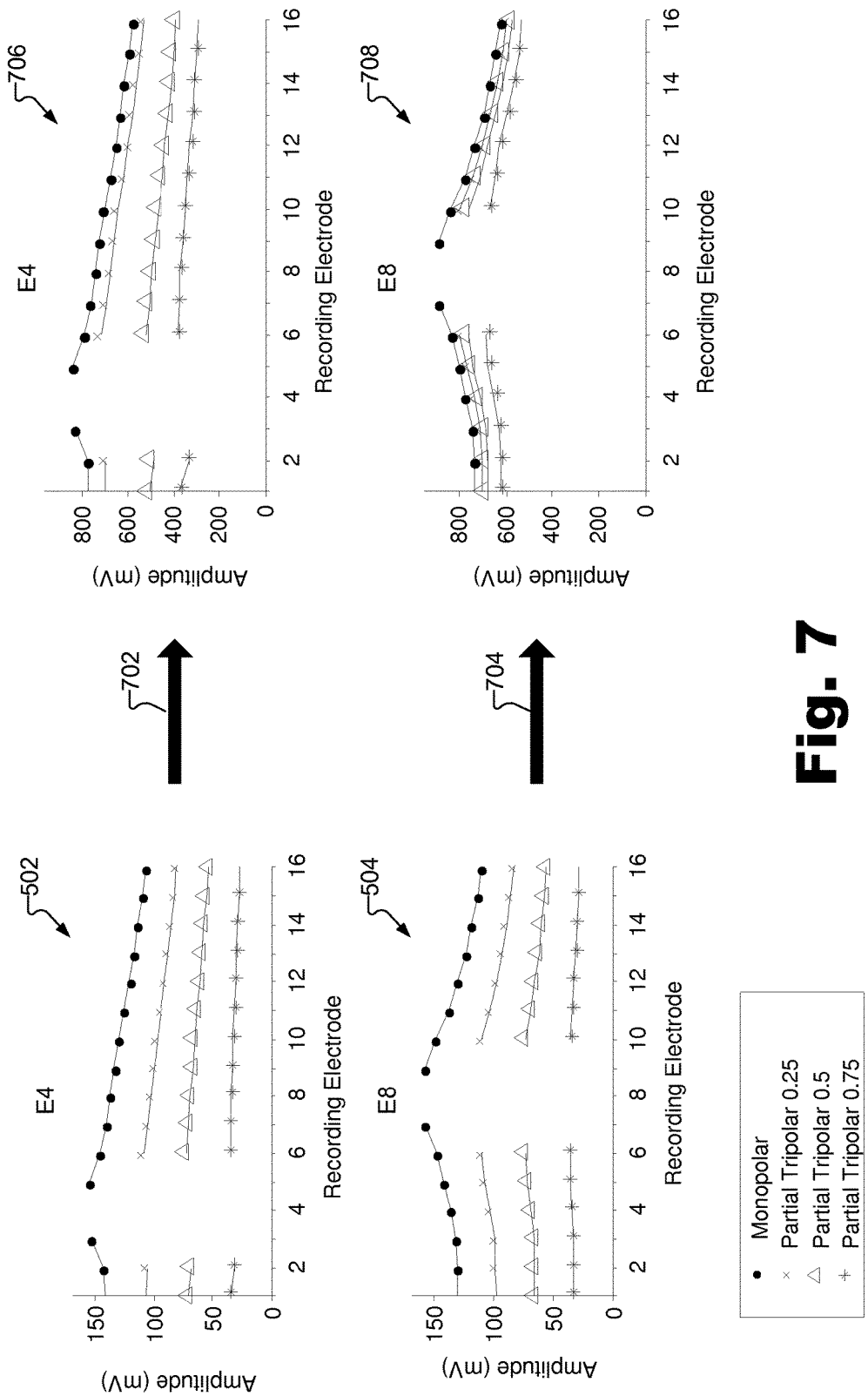

FIG. 7 illustrates an exemplary scaling of the EFI data sets illustrated in FIG. 5 to M levels associated with each electrode (i.e., electrode 4 and electrode 9) and each stimulation configuration. Arrow 702 represents the scaling of the EFI data sets illustrated in graph 502 and arrow 704 represents the scaling of the EFI data sets illustrated in graph 504. Graph 706 shows scaled EFI data sets corresponding to the EFI data sets shown in graph 502, and graph 708 shows scaled EFI data sets corresponding to the EFI data sets shown in graph 504. The lines shown in graphs 706 and 708 correspond to the lines shown in graphs 502 and 504 that have the same symbols superimposed thereon.

Based on the EFI data (either the scaled or unscaled EFI data sets) obtained for a plurality of stimulation configurations, processing facility 402 may identify a stimulation configuration included in the plurality of stimulation configurations that focuses an electric field produced by current applied to the electrode more than any other stimulation configuration included in the plurality of stimulation configurations. This may be performed in any suitable manner.

For example, processing facility 402 may compare the scaled EFI data sets in order to determine which scaled EFI data set is lowest in amplitude. As described above, the stimulation configuration corresponding to the EFI data set with the lowest amplitude maximally reduces current spread across the electrode array (i.e., it maximally focuses the electric field generated by stimulation of the electrode).

Figure 8:
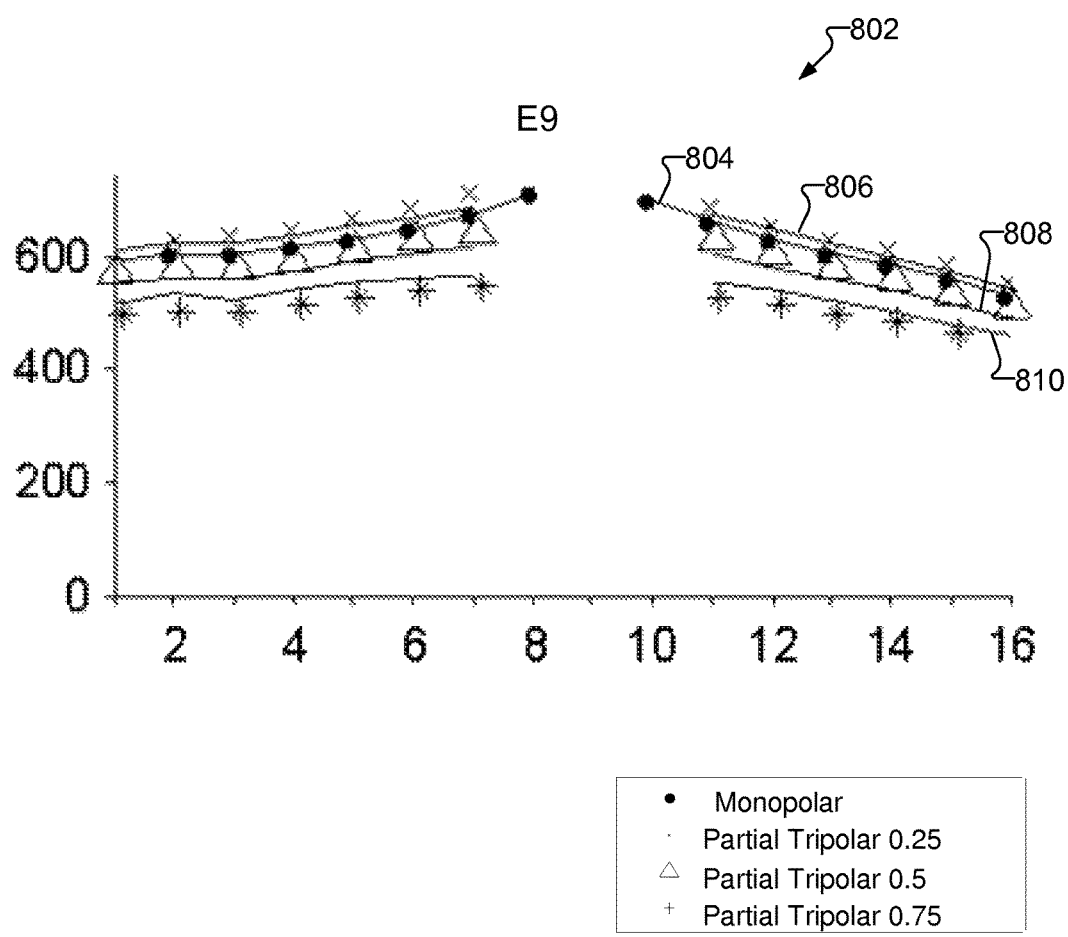

To illustrate, FIG. 8 shows an exemplary graph 802 exemplary scaled EFI data sets for a particular electrode included in an intracochlear electrode array and that is labeled "E9". The scaled EFI data sets represented in graph 802 correspond to the same stimulation configurations used in the examples of FIGS. 5 and 7. In particular, the scaled EFI data set corresponding to the monopolar stimulation configuration is represented in FIG. 8 by line 804, the scaled EFI data set corresponding to the first partial tripolar stimulation configuration is represented in FIG. 8 by line 806, the scaled EFI data set corresponding to the second partial tripolar stimulation configuration is represented in FIG. 8 by line 808, and the scaled EFI data set corresponding to the third partial tripolar stimulation configuration is represented in FIG. 8 by line 810.

In this particular example, the scaled EFI data set corresponding to the third partial tripolar stimulation configuration (i.e., the scaled EFI data set represented by line 810) is lower in amplitude than each of the other scaled EFI data sets represented in graph 802. Processing facility 402 may accordingly identify the third partial tripolar stimulation configuration as the stimulation configuration that maximally focuses an electric field produced by current applied to electrode E9. In response, programming facility 404 may direct the cochlear implant system of which electrode E9 is a part to use the third partial tripolar stimulation configuration for electrode E9 during a normal operation of the cochlear implant system, as will be described in more detail below.

Figure 9:
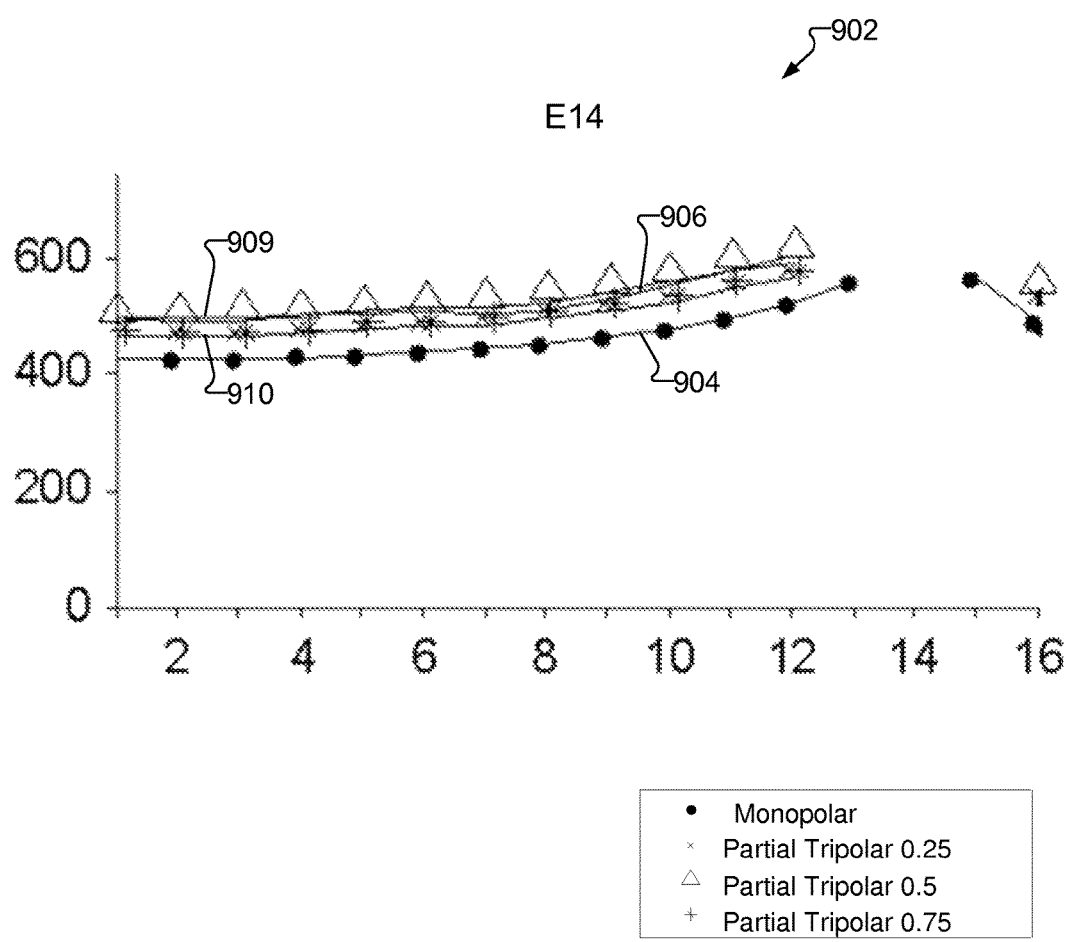

Continuing with this example, FIG. 9 shows an exemplary graph 902 exemplary scaled EFI data sets for an electrode labeled "E14" and that is included in the same intracochlear electrode array that includes electrode E9. The scaled EFI data sets represented in graph 902 correspond to the same stimulation configurations used in the previous examples. In particular, the scaled EFI data set corresponding to the monopolar stimulation configuration is represented in FIG. 9 by line 904, the scaled EFI data set corresponding to the first partial tripolar stimulation configuration is represented in FIG. 9 by line 906, the scaled EFI data set corresponding to the second partial tripolar stimulation configuration is represented in FIG. 9 by line 908, and the scaled EFI data set corresponding to the third partial tripolar stimulation configuration is represented in FIG. 9 by line 910.

In this particular example, the scaled EFI data set corresponding to the monopolar stimulation configuration (i.e., the scaled EFI data set represented by line 904) is lower in amplitude than each of the other scaled EFI data sets represented in graph 902. Processing facility 402 may accordingly identify the monopolar stimulation configuration as the stimulation configuration that maximally focuses an electric field produced by current applied to electrode E14. In response, programming facility 404 may direct the cochlear implant system of which electrode E14 is a part to use the monopolar stimulation configuration for electrode E14 during a normal operation of the cochlear implant system (even though the cochlear implant system has been programmed to use the third partial tripolar stimulation configuration for electrode E9).

Processing facility 402 may determine which stimulation configuration maximally reduces current spread in any other suitable manner. For example, processing facility 402 may compare the scaled EFI data sets in order to determine which scaled EFI data set has the lowest gradient or slope. The stimulation configuration corresponding to the EFI data set with the lowest gradient or slope may be identified as maximally reducing current spread across the electrode array. Other comparisons may be made in order to identify the optimal stimulation configuration as may serve a particular implementation.

In some examples, processing facility 402 may present one or more GUIs by way of a display device (e.g., a display screen associated with a computing device). The one or more GUIs may facilitate manual selection by a user (e.g., a clinician) of a particular stimulation configuration for a particular electrode. For example, processing facility 402 may present an EMI map representative of electric field imaging data for a plurality of stimulation configurations by way of the display device. The EMI map may be similar to any of the graphs shown in FIGS. 5-8, for example.

Returning to FIG. 4, as mentioned, programming facility 404 may direct a cochlear implant system to use an identified stimulation configuration for an electrode during a normal operation of the cochlear implant system. In other words, programming facility 404 may direct the cochlear implant system to use the identified stimulation configuration for the electrode while the cochlear implant system is applying electrical stimulation representative of audio content presented to the patient. It will be recognized that the operations described above as being performed by processing facility 402 may also be performed during normal operation of the cochlear implant system, during a fitting session in which the cochlear implant system is fitted to the patient, during a calibration session in which the cochlear implant system is calibrated, and/or at any other time as may serve a particular implementation.

The cochlear implant system may use the identified stimulation configuration for the electrode in any suitable manner. For example, the cochlear implant system may apply stimulation representative of audio content presented to the patient to the electrode in accordance with the identified stimulation configuration.

Figure 10:
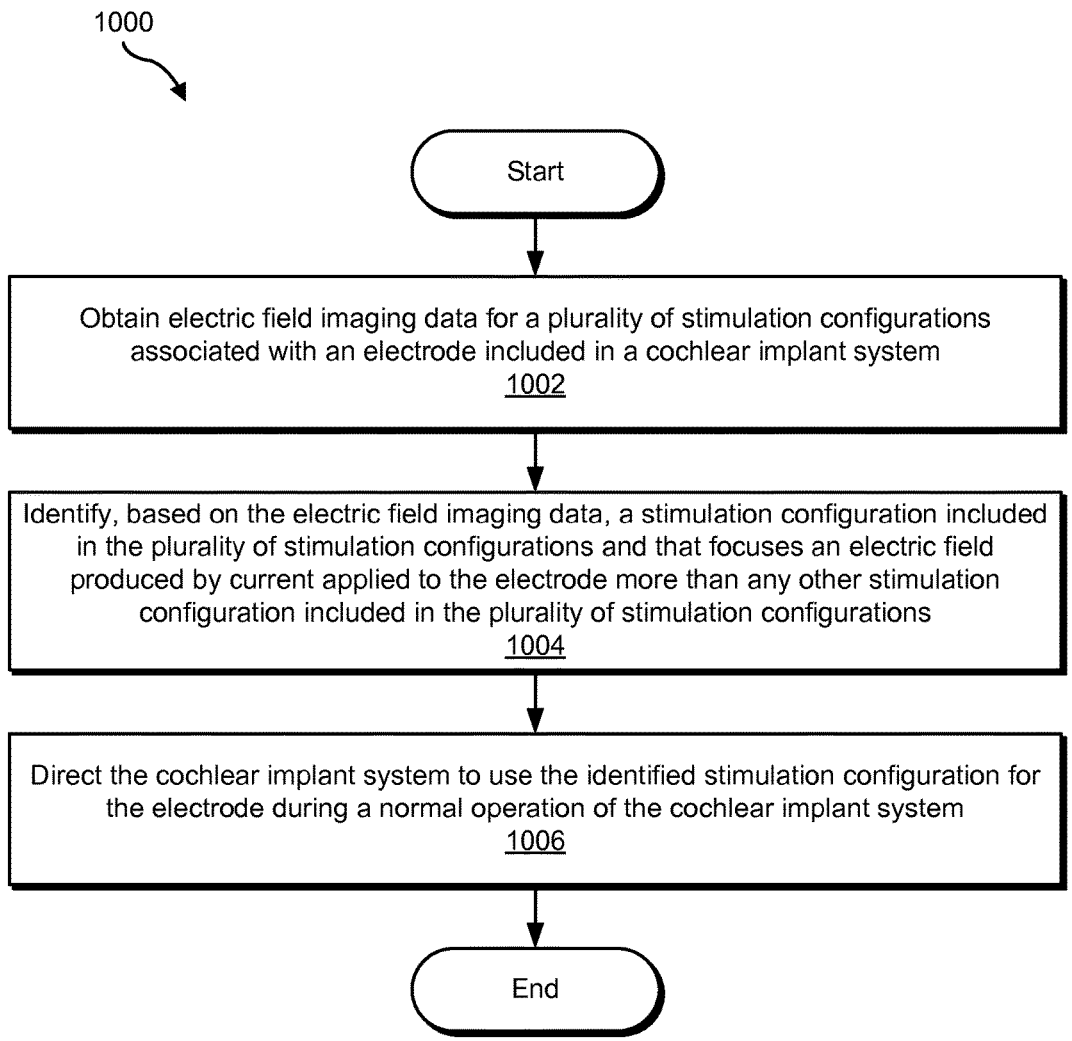
FIG. 10 illustrates an exemplary stimulation configuration management method according to principles described herein.

FIG. 10 illustrates an exemplary stimulation configuration management method 1000. While FIG. 10 illustrates exemplary steps according to one embodiment, other embodiments may omit, add to, reorder, and/or modify any of the steps shown in FIG. 10. One or more of the steps shown in FIG. 10 may be management system 400 and/or any implementation thereof.

In step 1002, a stimulation configuration management system obtains electric field imaging data for a plurality of stimulation configurations associated with an electrode included in a cochlear implant system. Step 1002 may be performed in any of the ways described herein.

In step 1004, the stimulation configuration management system identifies, based on the electric field imaging data, a stimulation configuration included in the plurality of stimulation configurations and that focuses an electric field produced by current applied to the electrode more than any other stimulation configuration included in the plurality of stimulation configurations. Step 1004 may be performed in any of the ways described herein.

In step 1006, the stimulation configuration management system directs the cochlear implant system to use the identified stimulation configuration for the electrode during a normal operation of the cochlear implant system. Step 1006 may be performed in any of the ways described herein.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 11:
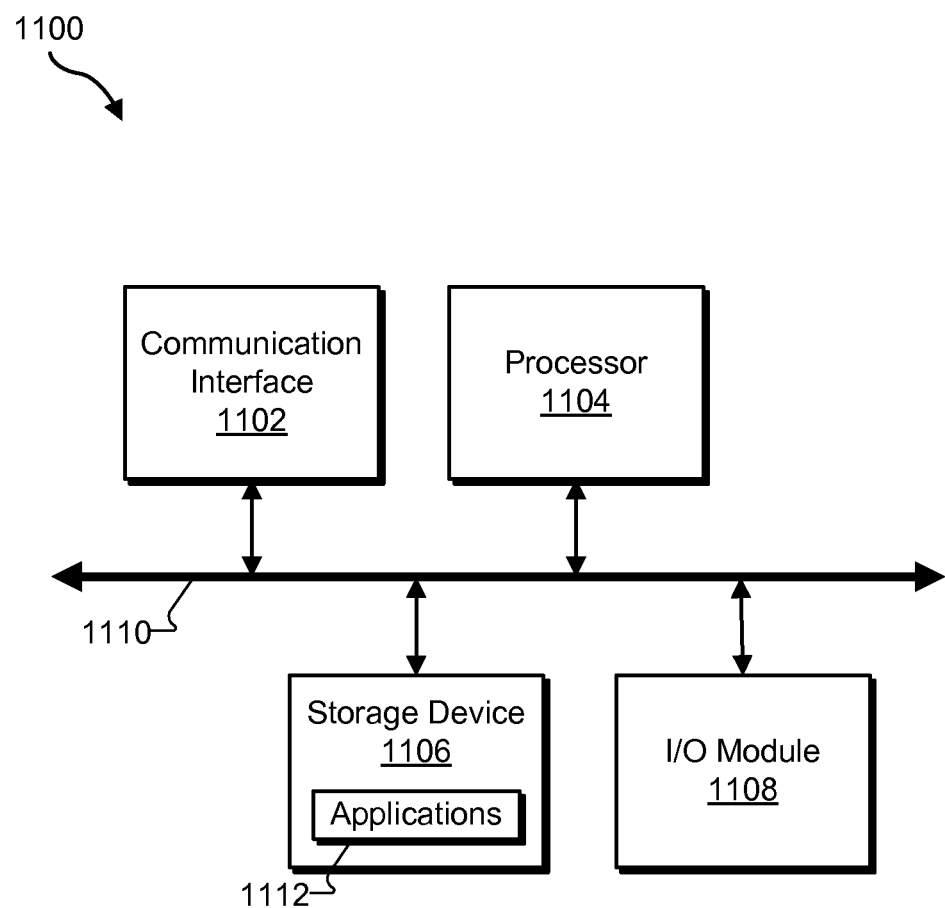
FIG. 11 illustrates an exemplary computing device according to principles described herein.

FIG. 11 illustrates an exemplary computing device 1100 that may be configured to perform one or more of the processes described herein. As shown in FIG. 11, computing device 1100 may include a communication interface 1102, a processor 1104, a storage device 1106, and an input/output ("I/O") module 1108 communicatively connected via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data or interpreting, executing, and/or directing execution of one or more of the instructions, processes, and/or operations described herein. Processor 1104 may direct execution of operations in accordance with one or more applications 1112 or other computer-executable instructions such as may be stored in storage device 1106 or another computer-readable medium.

Storage device 1106 may include one or more data storage media, devices, or configurations and may employ any type, form, and combination of data storage media and/or device. For example, storage device 1106 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1106. For example, data representative of one or more executable applications 1112 configured to direct processor 1104 to perform any of the operations described herein may be stored within storage device 1106. In some examples, data may be arranged in one or more databases residing within storage device 1106.

I/O module 1108 may be configured to receive user input and provide user output and may include any hardware, firmware, software, or combination thereof supportive of input and output capabilities. For example, I/O module 1108 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1108 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the facilities and/or systems described herein may be implemented by or within one or more components of computing device 1100. For example, one or more applications 1112 residing within storage device 1106 may be configured to direct processor 1104 to perform one or more processes or functions associated with any of the facilities and/or systems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    a processing facility that
        obtains electric field imaging data for a plurality of stimulation configurations associated with an electrode included in an intracochlear electrode array that is a part of a cochlear implant system configured for use by a patient, the plurality of stimulation configurations associated with the electrode comprising a monopolar stimulation configuration for the electrode and one or more multipolar stimulation configurations for the electrode, and
        identifies, based on the electric field imaging data, a stimulation configuration included in the plurality of stimulation configurations and that focuses an electric field produced by current applied to the electrode more than any other stimulation configuration included in the plurality of stimulation configurations; and a programming facility communicatively coupled to the processing facility and that directs, in response to the identification of the stimulation configuration that focuses the electric field produced by current applied to the electrode more than any other stimulation configuration included in the plurality of stimulation configurations, the cochlear implant system to use the identified stimulation configuration for the electrode during a normal operation of the cochlear implant system.

2. The system of claim 1, wherein the processing facility obtains the electric field imaging data by:

directing a cochlear implant included in the cochlear implant system to apply a stimulation pulse to the electrode using a first stimulation configuration included in the plurality of stimulation configurations; and recording an intracochlear potential that occurs in response to the stimulation pulse at each of a remaining number of electrodes included in the intracochlear electrode array to obtain a first electric field data set corresponding to the first stimulation configuration.

3. The system of claim 2, wherein the processing facility further obtains the electric field imaging data by applying a linear model to the first electric field data set to determine a second electric field data set corresponding to a second stimulation configuration included in the plurality of stimulation configurations.

4. The system of claim 3, wherein the stimulation pulse has a fixed amplitude, and wherein the processing facility further obtains the electric field imaging data by:

scaling the first electric field data set to a first most comfortable level ("M level") associated with both the electrode and the first stimulation configuration; and scaling the second electric field data set to a second M level associated with both the electrode and the second stimulation configuration.

5. The system of claim 4, wherein the processing facility identifies the stimulation configuration that focuses the electric field more than any other stimulation configuration included in the plurality of stimulation configurations by comparing the scaled first electric field data set to the scaled second electric field data set, wherein:

if the scaled first electric field data set is lower in amplitude than the scaled second electric field data set, the processing facility identifies the first stimulation configuration as being the stimulation configuration that focuses the electric field more than any other stimulation configuration included in the plurality of stimulation configurations; and if the scaled second electric field data set is lower in amplitude than the scaled first electric field data set, the processing facility identifies the second stimulation configuration as being the stimulation configuration that focuses the electric field more than any other stimulation configuration included in the plurality of stimulation configurations.

6. The system of claim 4, wherein the processing facility identifies the stimulation configuration that focuses the electric field more than any other stimulation configuration included in the plurality of stimulation configurations by comparing the scaled first electric field data set to the scaled second electric field data set, wherein:

if a gradient of the scaled first electric field data set is lower than a gradient of the scaled second electric field data set, the processing facility identifies the first stimulation configuration as being the stimulation configuration that focuses the electric field more than any other stimulation configuration included in the plurality of stimulation configurations; and if the gradient of the scaled second electric field data set is lower than the gradient of the scaled first electric field data set, the processing facility identifies the second stimulation configuration as being the stimulation configuration that focuses the electric field more than any other stimulation configuration included in the plurality of stimulation configurations.

7. The system of claim 4, wherein the processing facility determines the first and second M levels prior to scaling the first electric field data set to the first M level and prior to scaling the second electric field data set to the second M level.

8. The system of claim 7, wherein the processing facility objectively determines the first and second M levels based on an evoked response that occurs in response to stimulation of the electrode.

9. The system of claim 2, wherein the processing facility further obtains the electric field imaging data by:

directing the cochlear implant included in the cochlear implant system to apply an additional stimulation pulse to the electrode using a second stimulation configuration included in the plurality of stimulation configurations; and recording an additional intracochlear potential that occurs in response to the additional stimulation pulse at each of the remaining number of electrodes included in the intracochlear electrode array to obtain a second electric field data set corresponding to the second stimulation configuration.

10. The system of claim 2, wherein the first stimulation configuration is the monopolar stimulation configuration.

11. The system of claim 1, wherein:

the processing facility
obtains additional electric field imaging data for an additional plurality of stimulation configurations associated with an additional electrode included in the intracochlear electrode array, and identifies, based on the additional electric field imaging data, an additional stimulation configuration included in the additional plurality of stimulation configurations and that focuses an electric field produced by current applied to the additional electrode more than any other stimulation configuration included in the additional plurality of stimulation configurations; and the programming facility directs the cochlear implant system to use the identified additional stimulation configuration for the additional electrode during the normal operation of the cochlear implant system.

12. The system of claim 11, wherein the identified additional stimulation configuration is different than the identified stimulation configuration.

13. The system of claim 1, further comprising the cochlear implant system, wherein the cochlear implant system uses the identified stimulation configuration for the electrode during the normal operation of the cochlear implant system by applying stimulation representative of audio content presented to the patient to the electrode in accordance with the identified stimulation configuration.

14. The system of claim 1, wherein the processing facility presents an electric field imaging map representative of the electric field imaging data for the plurality of stimulation configurations by way of a display device.

15. A system comprising:
a cochlear implant system that comprises a sound processor, a cochlear implant, and an intracochlear electrode array coupled to the cochlear implant; and
a fitting system communicatively coupled to the cochlear implant system by way of the sound processor and that
obtains a first electric field imaging data set for a monopolar stimulation configuration associated with an electrode included in the intracochlear electrode array,
obtains a second electric field imaging data set for a multipolar stimulation configuration associated with the electrode,
scales the first electric field data set to a most comfortable level ("M level") associated with both the electrode and the monopolar stimulation configuration,
scales the second electric field data set to a second M level associated with both the electrode and the multipolar stimulation configuration, and
compares the scaled first electric field data set to the scaled second electric field data set to determine which of the monopolar stimulation configuration and the multipolar stimulation configuration maximally focuses an electric field produced by current applied to the electrode;
wherein
if the scaled first electric field data set is lower in amplitude than the scaled second electric field data set, the fitting system determines that the monopolar stimulation configuration maximally focuses the electric field compared to the multipolar configuration and directs, in response to the determination that the monopolar stimulation configuration maximally focuses the electric field compared to the multipolar configuration, the cochlear implant system to use the monopolar stimulation configuration for the electrode during a normal operation of the cochlear implant system, and
if the scaled second electric field data set is lower in amplitude than the scaled first electric field data set, the fitting system determines that the multipolar stimulation configuration maximally focuses the electric field compared to the monopolar configuration and directs, in response to the determination that the multipolar stimulation configuration maximally focuses the electric field compared to the monopolar configuration, the cochlear implant system to use the multipolar stimulation configuration for the electrode during the normal operation of the cochlear implant system.

16. A method comprising:
obtaining, by a stimulation configuration management system, electric field imaging data for a plurality of stimulation configurations associated with an electrode included in a cochlear implant system, the plurality of stimulation configurations associated with the electrode comprising a monopolar stimulation configuration for the electrode and one or more multipolar stimulation configurations for the electrode;
identifying, by the stimulation configuration management system based on the electric field imaging data, a stimulation configuration included in the plurality of stimulation configurations and that focuses an electric field produced by current applied to the electrode more than any other stimulation configuration included in the plurality of stimulation configurations; and
directing, by the stimulation configuration management system in response to the identifying of the stimulation configuration that focuses the electric field produced by current applied to the electrode more than any other stimulation configuration included in the plurality of stimulation configurations, the cochlear implant system to use the identified stimulation configuration for the electrode during a normal operation of the cochlear implant system.

17. The method of claim 16, wherein the obtaining comprises:
directing a cochlear implant included in the cochlear implant system to apply a stimulation pulse to the electrode using a first stimulation configuration included in the plurality of stimulation configurations; and
recording an intracochlear potential that occurs in response to the stimulation pulse at each of a remaining number of electrodes included in the intracochlear electrode array to obtain a first electric field data set corresponding to the first stimulation configuration.

18. The method of claim 17, wherein the obtaining further comprises applying a linear model to the first electric field data set to determine a second electric field data set corresponding to a second stimulation configuration included in the plurality of stimulation configurations.

19. The method of claim 18, wherein the stimulation pulse has a fixed amplitude, and wherein the obtaining further comprises:
scaling the first electric field data set to a first most comfortable level ("M level") associated with both the electrode and the first stimulation configuration; and
scaling the second electric field data set to a second M level associated with both the electrode and the second stimulation configuration.

* * * * *